United States Patent
Voznesensky et al.

(10) Patent No.: US 6,567,696 B2
(45) Date of Patent: May 20, 2003

(54) PHYSIOTHERAPEUTIC DEVICE

(75) Inventors: Boris Voznesensky, Herzlia (IL); Isaac Segev, Ra'anana (IL)

(73) Assignee: MediSeb Ltd., Herzlia (IL)

( * ) Notice: Subject to any disclaimer, the term of this patent is extended or adjusted under 35 U.S.C. 154(b) by 108 days.

(21) Appl. No.: 09/776,878

(22) Filed: Feb. 6, 2001

(65) Prior Publication Data

US 2002/0107543 A1 Aug. 8, 2002

(51) Int. Cl.⁷ .............................. A61F 7/00; A61N 1/00
(52) U.S. Cl. ............................................. 607/3; 607/108
(58) Field of Search ................... 607/3, 108, 96–114; 606/112

(56) References Cited

U.S. PATENT DOCUMENTS

| | | |
|---|---|---|
| 3,133,539 A | 5/1964 | Eidus |
| 3,168,895 A | 2/1965 | Motoharu Okuharar |
| 3,207,159 A | 9/1965 | Kazuma Tateisi |
| 4,585,002 A | 4/1986 | Kissin |
| 4,640,284 A | 2/1987 | Ruderian |
| 4,676,246 A * | 6/1987 | Korenaga ............... 607/153 |
| 4,860,748 A | 8/1989 | Chiurco et al. |
| 4,915,108 A | 4/1990 | Sun |
| 5,097,828 A | 3/1992 | Deutsch |
| 5,169,384 A | 12/1992 | Bosniak et al. |
| 5,336,255 A | 8/1994 | Kanare et al. |
| 5,601,618 A | 2/1997 | James |
| 5,766,236 A * | 6/1998 | Detty et al. ............ 607/149 |
| 6,021,348 A * | 2/2000 | James ....................... 607/3 |
| 6,438,428 B1 * | 8/2002 | Axelgaard et al. ...... 607/152 |
| 2002/0026226 A1 * | 2/2002 | Ein ........................ 607/108 |

FOREIGN PATENT DOCUMENTS

DE 3326429 * 1/1985

* cited by examiner

Primary Examiner—John A. Jeffery
(74) Attorney, Agent, or Firm—G. E. Ehrlich Ltd.

(57) ABSTRACT

A physiotherapeutic device for concurrently applying heat and electrical stimulation to a localized treatment area comprises a heat transfer medium for placing in contact with the treatment area, the heat transfer medium having a heat capacity such that the device is operable to change a temperature of said heat transfer medium from a temperature able to induce a burn to a safe temperature substantially within a minute.

21 Claims, 4 Drawing Sheets

PHYSIOTHERAPEUTIC DEVICE

FIELD OF THE INVENTION

The present invention relates to a physiotherapeutic device and more particularly but not exclusively to devices for providing both electrotherapeutic and thermotherapeutic treatment in combination.

BACKGROUND OF THE INVENTION

The use of heat and cold for therapeutic purposes is well known. Hot water bags, ice packs, and the like have commonly been used to alleviate pain, to stimulate the flow of blood, or to restrict the flow of blood beneath the surface of the skin. One of the problems with hot water bags is that the temperature steadily decreases during use, thereby necessitating refilling them with a heated liquid. Ice packs steadily increase in temperature when applied to the skin, and ice must accordingly be added from time to time if a cold temperature is to be maintained. It is also difficult to regulate the temperature of an ice pack or a hot water bottle such that it is neither too cold nor too hot when applied to the skin.

A number of therapeutic devices have been developed which employ Peltier thermoelectric units for providing heat or cold. Such devices include switches which allow reversing the polarity of the current passing through the thermoelectric units, thereby determining whether a hot or a cold stimulus is to be applied thereby. U.S. Pat. No. 3,207,159 discloses such a device which includes a probe for heating or cooling selected cutaneous points. U.S. Pat. Nos. 4,585,002 and 4,860,748 disclose devices which employ microprocessors for controlling the duration and/or intensity of heat and cold generated by Peltier thermoelectric units. U.S. Pat. Nos. 3,133,539, 3,168,895, 4,640,284 and 4,915,108 disclose various other therapeutic devices for applying heat or cold to the skin.

Therapeutic electrical stimulation of soft body tissue is well known. These devices which produce transcutaneous electrical nerve stimulation are known as TENS devices and are used to both relieve chronic pain and to produce muscle building stimulation.

As mentioned above, it is also well known to treat injured and weakened soft body tissue through the use of the topical application of heating atop the body tissue to be treated.

Specifically, devices beginning with the earliest of the resistive wire heating pads are well known in the art to accomplish the individual function of heating. The more recently developed TENS units are well known for therapeutic electrical stimulation of muscles and soft body tissue. A more complex therapeutic device for providing either one of heating and cooling of the skin and underlying body tissue is disclosed in U.S. Pat. No. 5,097,828 invented by Deutsch. This device includes a handle and a thermally conductive head which utilizes Peltier effect devices for heating or cooling a contact plate within the head. The contact plate may also be connected to a high-voltage source for electrical stimulation.

In U.S. Pat. No. 5,336,255, Kanare et al. have disclosed an electrical stimulation and heating or cooling pack which includes a nonconductive pouch and straps for positioning and holding the pouch against a body part. Flexible conductive patches attached to the pouch are connectable to a remote pulse generator. An electrically conductive adhesive gel pad is also provided for coupling the conductive patch to the body part. By this arrangement, both heating or cooling and electrical stimulation of a body part are provided.

U.S. Pat. No. 5,601,618 discloses a very simple device for providing combination electrical stimulation or TENS-type soft body tissue stimulation and the simultaneous heating of the body tissue. The device is hermetically sealed and extremely compact and portable, relying upon low current dry battery power for heating and the utilization of double-sided adhesive conductive electrodes which adhesively attach to the skin area over the soft body tissue for supporting the device against the skin during use.

A combination soft body tissue stimulator and heating device includes a thin, flat, molded flexible plastic pad, one side of which defines a working surface. The molded pad has a plurality or an array of spaced separate conductive areas each having an exposed conductive surface, being generally coplanar with the working surface. When the device is properly installed, each conductive area makes electrical contact with, and receives support from, a separate disposable double-sided flexible adhesive electrode attached to the skin over the soft tissue. The array of electrodes adhesively attached to the skin is generally aligned with the array of conductive areas of the pad so that only the adhesive attachment between the conductive areas and the electrodes is required to hold the device in place against the skin. A resistive heating element is embedded within the pad, which pad is generally coextensive with and electrically isolated from the array of conductive areas on the side thereof away from the working surface. The conductive areas are connectable to a pulsed electrical current and the heating element is connectable to a D.C. battery supply for simultaneous stimulation and heating of any desired soft body tissue area.

A particular use for treatments of this type is in relation to post-surgical trauma and trauma resulting from, for example, sports-related injuries, this being a common occurrence with which patients must regularly contend. The trauma often manifests itself in the form of swelling which results from the accumulation of bodily fluids underlying the skin adjacent to the site of the trauma. Such swelling not only results in patient discomfort, but also inhibits recovery, as it results in an increased application of pressure against the tissue and surrounding nerve and organ structures. Furthermore, such swelling reduces patient mobility when the trauma is of an orthopedic nature. For all of the foregoing reasons, it is a common objective of health care professionals to reduce the accumulation of undesired fluid underlying the site of patient trauma as soon as possible. To date, such fluid reducing measures have typically encompassed the application of cold compresses such as ice packs for prescribed periods of time to the site of the trauma, followed by the application of hot compresses.

As discussed above, non-powered cooling solutions such as cold compresses are oftentimes initially too cold for the patient to comfortably tolerate and, as a result, the patient is unable to tolerate the cooling effects of the compresses for the prescribed period of time. Furthermore, because the compresses remove heat from the body, the temperature of the compresses themselves progressively increases, thereby diminishing their temperature reducing affects. Longer periods of cooling can be provided by increasing the amount of coolant such as ice in the cold compress; however, such practices increase the size of the compress, thereby adversely impacting upon the compresses' ability to conform to the site of the trauma and compromising their effectiveness in removing heat from the site of the injury.

An optimal regimen for reducing tissue swelling provides for treatment with cold compresses for up to about 72 hours followed by warm compress treatment for a period of about 10–14 days. Furthermore, because water has a high specific gravity, the provision of additional quantities of ice in the cold compress further increases the downward pressure exerted against the trauma site, thereby negating to some extent the benefits afforded by cold compress treatment. Further problems arise as a result of the considerable time demands of personnel at health care facilities, as the cold and hot compresses used in such facilities often times cannot be properly monitored and changed prior to loss of their effectiveness, particularly during overnight and prolonged stays.

As a result of all of the foregoing deficiencies in the prior art, patient recovery from physical trauma surgery and inflammation is often prolonged, resulting in increased patient discomfort, lack of motility in instances of orthopedic trauma, and prolonged periods of patient medication resulting from discomfort arising from the trauma and the prolonged presence of subcutaneous swelling.

As discussed above, patient recovery from trauma can be expedited by the application of transcutaneous electrical neurostimulation (TENS), which typically involves the application of an alternating current (AC) potential to the tissue by way of two or more electrodes of opposite polarity U.S. Pat. No. 5,169,384 to Bosniak et al, discloses a temperature variable and iontophoretic device for application to the body of a patient, which has an outer support member coupled to a device for selectively applying thermal energy to the body of a patient or for removing thermal energy therefrom, and a further device for selectively energizing the thermal energy supply and removal device. Another member is coupled to the outer support member for iontophoretically administering a compound to the body of the patient. The energizing device comprises a user-operable data input device, which also controls the iontophoretic administering device. Transcutaneous electrical neurostimulation (TENS) can also be provided.

Heat or cooling based treatment is particularly effective at reducing pain, as discussed above, but advantageous levels of heating or cooling may easily cause burns if the heat source is not removed within an appropriate amount of time. The appropriate amount of time varies depending on the temperature deemed necessary in the treatment and thus renders the type of treatment unsuitable for unsupervised use by a patient. Both unpowered and powered treatment devices have to be removed from the treatment site before a burn appears.

Furthermore, the above combination devices, that provide both thermal and electrical treatment, do not apply point electrical stimulation to a point within the area of the thermal stimulation because the heat pad cannot serves as both of the two required electrodes.

It is an aim of the present invention to provide a treatment device that is simple and safe to use unsupervised by a patient in view of all of the aforementioned problems and which can provide localized electrical and thermal stimulation together to a small localized region.

SUMMARY OF THE INVENTION

According to a first aspect of the present invention there is thus provided a physiotherapeutic device for concurrently providing heat transfer and electrical stimulation to a localized treatment area, the device comprising:

a heat transfer medium for placing in contact with said treatment area, said heat transfer medium comprising a thermo-conductive material and having a heat capacity such that said device is operable to change a temperature gradient within of said heat transfer medium from one able to induce a burn to a safe temperature substantially within a minute, at least one electrode located within said heat transfer medium, said electrode comprising a thermo-conductive material, and a dielectric layer for providing electrical isolation between said electrodes and said heat transfer medium, said dielectric layer comprising a thermo-conductive material. Preferably the heat transfer is bi-directional although embodiments are envisaged which are solely for heating or solely for cooling.

Preferably, the heat transfer medium has an external dielectric covering.

Preferably, the electrodes are thermally coupled to said heat transfer medium via said dielectric layer.

A preferred embodiment has a temperature range of at least 40 degrees between a maximum treatment temperature and a minimum treatment temperature, and being operable to permit said heat transfer medium to alternate between said maximum and said minimum treatment temperatures in substantially one minute.

A preferred embodiment has a plurality of electrodes integrally located within said heat transfer medium.

In a preferred embodiment, each electrode is programmable independently to provide electrical stimulation.

Preferably, said electrodes and said heat transfer medium are programmable separately to provide a combined regime of electrical and heat treatment.

Preferably, the electrodes are programmable to provide electrical stimulation selectably as a constant voltage level, a constant current level, and a selectable waveform at a selectable frequency.

Preferably, the device is programmable remotely over an electronic network.

Preferably, the electrode has a thermal diffusivity substantially similar to a thermal diffusivity of said heat transfer medium.

According to a second aspect of the present invention there is provided a physiotherapeutic device for concurrently applying heat, cooling, and electrical stimulation to a localized treatment area, the device comprising a heat transfer medium for placing in contact with said treatment area and at least two electrodes integrally located within said heat transfer medium and electrically insulated therefrom.

A device according to the invention preferably has a dielectric layer intervening between at least one electrode and said heat transfer medium.

Preferably, the device has a temperature range of at least 40 degrees between a maximum treatment temperature and a minimum treatment temperature, and having a combination of heat control power, heat transfer medium size and heat transfer medium thermal diffusivity selected to permit said heat transfer medium to alternate between said maximum and said minimum treatment temperatures in substantially one minute.

Preferably, the device has a plurality of electrodes, each electrode being programmable independently to provide electrical stimulation.

Preferably, the electrodes and said heat transfer medium are programmable separately to provide a combined regime of electrical and heat treatment.

Preferably, the electrodes are programmable to provide electrical stimulation selectably as a constant voltage level, a constant current level, and a selectable waveform at a selectable frequency.

Embodiments are preferably programmable remotely over an electronic network.

Preferably, the electrodes are thermally coupled to said heat transfer medium.

Preferably, the dielectric layer is a heat conducting layer.

Preferably, the heat conducting medium has an outer dielectric coating.

Preferably, the dielectric layer is a heat conducting layer.

According to a third aspect of the present invention there is provided a method of manufacturing a physiotherapeutic device, comprising the steps of providing a heat transfer medium having a low heat capacity, providing openings in said heat transfer medium, lining said openings with a dielectric material, and inserting electrodes through said lined openings.

Preferably, the dielectric material comprises a thermal conductor.

Preferably, the thermal conductor comprises aluminum oxide.

In an embodiment, the gaps are arranged circumferentially in said surface.

Typically the gaps may be arranged as segments in said surface.

Alternatively, the gaps may be arranged circumferentially around said surface.

As a further alternative, said gaps may be arranged successively outwardly radially around a center of said surface.

A preferred range for the separation between electrodes is between 5 and 50 mm.

According to a fourth aspect of the present invention there is provided a method of providing combined electrical and thermal stimulation to a treatment area, the method comprising the steps of:

applying to said treatment area an integral electrode and heat transfer medium comprising a plurality of electrodes arranged within a heat transfer medium, thermally coupled thereto and electrically insulated from one another, applying electrical stimulation via said electrodes, and applying thermal stimulation via said integral electrode and heat transfer medium.

Preferably, the thermal stimulation comprises changing a temperature of said surface by substantially 40 Celsius within substantially one minute.

The method preferably comprises providing changing voltages at at least one of said electrodes.

The method preferably comprises providing changing currents at at least one of said electrodes.

The method may also comprise providing independent waveforms to at least two of said electrodes.

Alternatively or additionally the method may comprise providing cyclical changes in a direction of thermal transfer over a treatment time.

Alternatively or additionally, the method comprises providing irregular cyclical changes over a treatment time.

Preferably, the method comprises applying said treatment to a plurality of treatment regions by using a plurality of integral electrode and heat transfer media, each applied to a different one of said plurality of treatment regions.

BRIEF DESCRIPTION OF THE DRAWINGS

For a better understanding of the invention and to show how the same may be carried into effect, reference will now be made, purely by way of example, to the accompanying drawings, in which.

DESCRIPTION OF THE PREFERRED EMBODIMENTS

Figure 1:
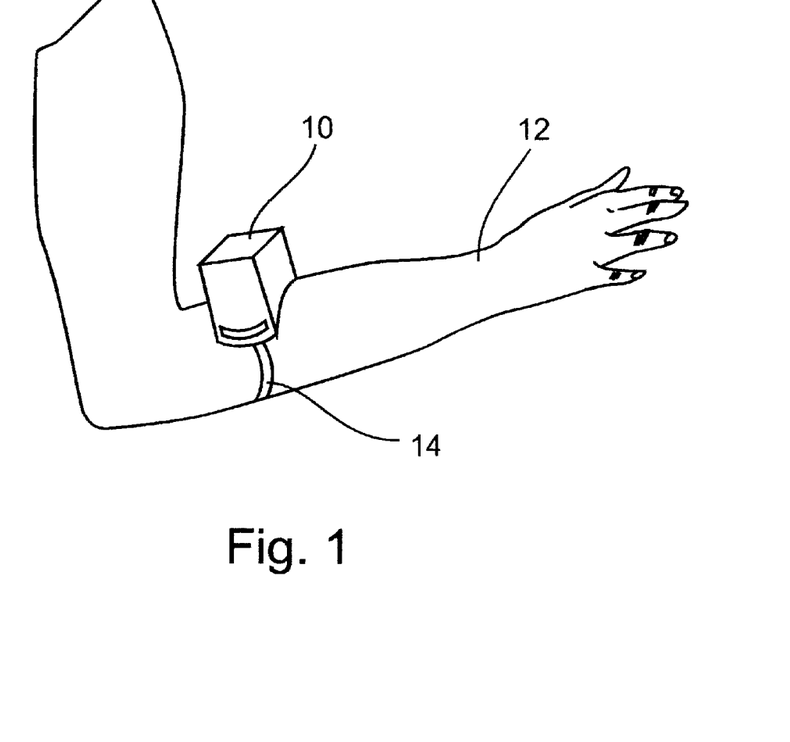
FIG. 1 is a generalized diagram showing a physiotherapeutic device according to an embodiment of the present invention being applied to a relatively small treatment area on an arm.

Reference is now made to FIG. 1, which is a simplified diagram showing a physiotherapeutic device 10 operative in accordance with a first embodiment of the present invention. The device 10 is attached to the arm 12 of a patient via a strap 14 such that a lower surface thereof is in contact with a treatment area of a patient. The treatment area may be relatively small and it is desirable to provide either one or both of an electrotherapeutic and a thermotherapeutic treatment to the treatment area. In particular the device is able, if required, to provide both electrotherapeutic and thermotherapeutic treatments to the same area simultaneously.

Figure 2:
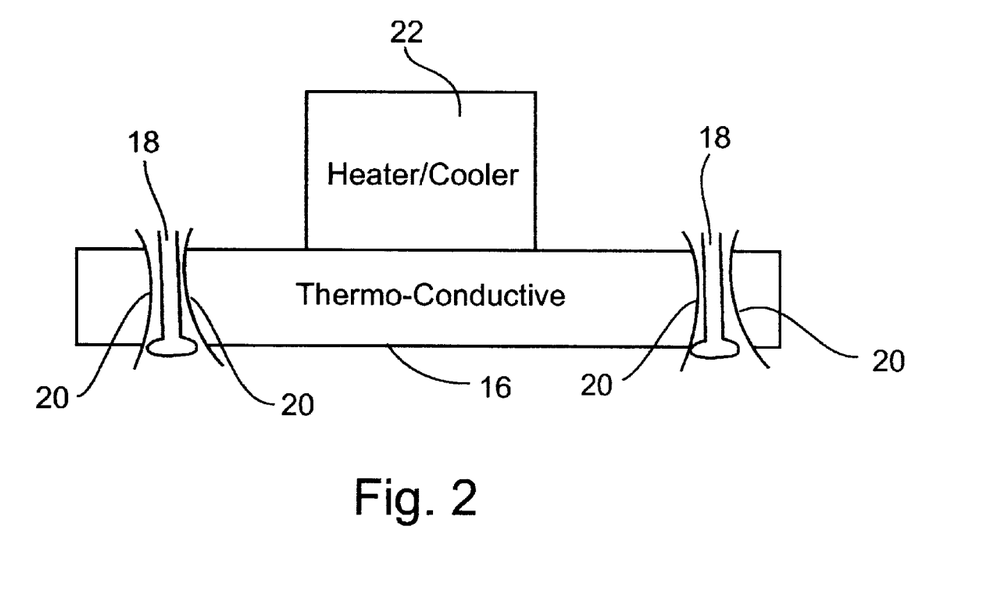
FIG. 2 is a generalized side view of the device of FIG. 1.

Reference is now made to FIG. 2 which is a simplified diagram showing in cross section a view of some of the elements of a device according to the embodiment of FIG. 1. The physiotherapeutic device 10 preferably comprises a heat transfer medium 16 which is placed in contact with the treatment area. The heat transfer medium preferably comprises an outer cover of thermo-conductive material, as will be discussed in further detail below. Inserted into openings in the heat transfer area 16 are electrodes 18, and the electrodes 18 are electrically isolated from the heat transfer area by respective dielectric layers 20. Preferably, the dielectric layers are selected such that they provide electrical isolation and at the same time allow thermal coupling so that, thermally, the electrode surface acts as a continuation of the heat transfer medium. A preferred material for the dielectric layers 20 is aluminum oxide although any material that combines good thermal conductivity with effective electrical isolation may be considered. Other particularly preferred materials include those known as In-Sil-8, Softface™ and Kon-Dux, and are manufactured by Aavid Thermal Products Ltd. and Silicon Wafer™ manufactured by Autronic Inc. The electrodes 18 generally comprise a narrow conductor which passes through the opening to broaden out into a flattened end 19. Both the dielectric layers 20 and the electrodes 18 are selected from materials having high thermal diffusivity.

The electrodes 18 preferably comprise a material having a heat capacity which is at least similar to that of the heat transfer medium 16. The heat transfer medium 16 itself preferably is selected to have a relatively low heat capacity, and more specifically a heat capacity such that the device is operable to change the temperature of the heat transfer medium from a temperature able to induce a burn in the treatment area with prolonged contact to a safe temperature, and to be able to carry out such a temperature change substantially within a minute. Herein a safe temperature means a temperature wherein even mild burn effects are not likely to occur following substantially continuous contact. Likewise the material of the heat transfer medium is selected to have a high thermal diffusivity.

Temperature levels are induced in the heat transfer medium by a temperature driving element 22, which is a combined heater and cooler and which is placed in thermal association with the heat transfer medium 16. The temperature driving element 22 will be described below in greater detail with respect to FIG. 3. The device is built to allow programmable, preferably bi-directional, heat transfer to and from a localized heat treatment area.

The outer surface of the heat transfer medium 16 preferably comprises a dielectric layer so as to cancel out possible electrode current paths through the heat transfer medium 16. This outer surface dielectric layer is also selected from materials having a high thermal diffusivity.

As shown in FIG. 2, electrodes 18 are integrally located within the heat transfer medium 16 in such a way as to serve as an extension of the heat transfer medium whilst at the same time being electrically isolated therefrom so that the respective electrodes 18 may operate at different polarities or using different programs without interfering with each other. Thus it is possible to apply a combined electrical and thermal treatment program to a small treatment area. A preferred distance between electrodes for effective operation is in a range of 5 to 50 mm.

Preferably, the temperature driving element 22 is able to operate the heat transfer medium over a temperature range of at least 40 degrees, preferably 50 degrees, between a maximum treatment temperature and a minimum treatment temperature. Preferably element 22 is sufficiently powerful to enable the surface 16 to alternate between the maximum and the minimum treatment temperatures, and corresponding heat transfer levels and directions in less than substantially one minute. In this way it is possible to provide a treatment program that alternates between high and low temperatures to provide extremes of temperature sufficiently large to alleviate pain without there being any risk of causing burns. The reduction in risk of burns is preferably achieved by regular alternation between high and low temperatures.

A typical minimum temperature for the heat transfer medium 16 and electrodes 18 may be in the region of −10 Celsius and a typical maximum temperature may be in the region of 42 Celsius.

A particularly preferred embodiment has the electrodes 18 arranged in pairs, and preferably has several such pairs. Each pair of electrodes is preferably programmable independently to provide different kinds of electrical stimulation as will be explained in more detail below. Again, preferably, the electrodes 18 and the heat transfer medium are programmable separately to provide a combined regime of electrical and heat treatment so that any one of a range of different heat treatments is independently combinable with any one of a range of electrical treatments.

Preferably, the electrodes, or electrode pairs, are programmable to provide electrical stimulation of different types. Available types may include a constant voltage level, a constant current level, and different shaped waveforms at various frequencies. A typical current level for such a device is preferably in the range of 1–70 mA.

Effective separation between electrodes 18 is within the range of 5 to 50 mm.

A particularly preferred embodiment comprises a connection for downloading programming instructions from a computer or from a telephone so that it is remotely programmable. In this way, a patient may take home a device set with a particular treatment program. At the end of a week the patient reports his progress by telephone or by e-mail or by any other remote communication means and a treatment supervisor is able to modify the device in the light of the patient's report, by e-mail or similar electronic means, without the patient being required to attend the treatment center.

Figure 3:
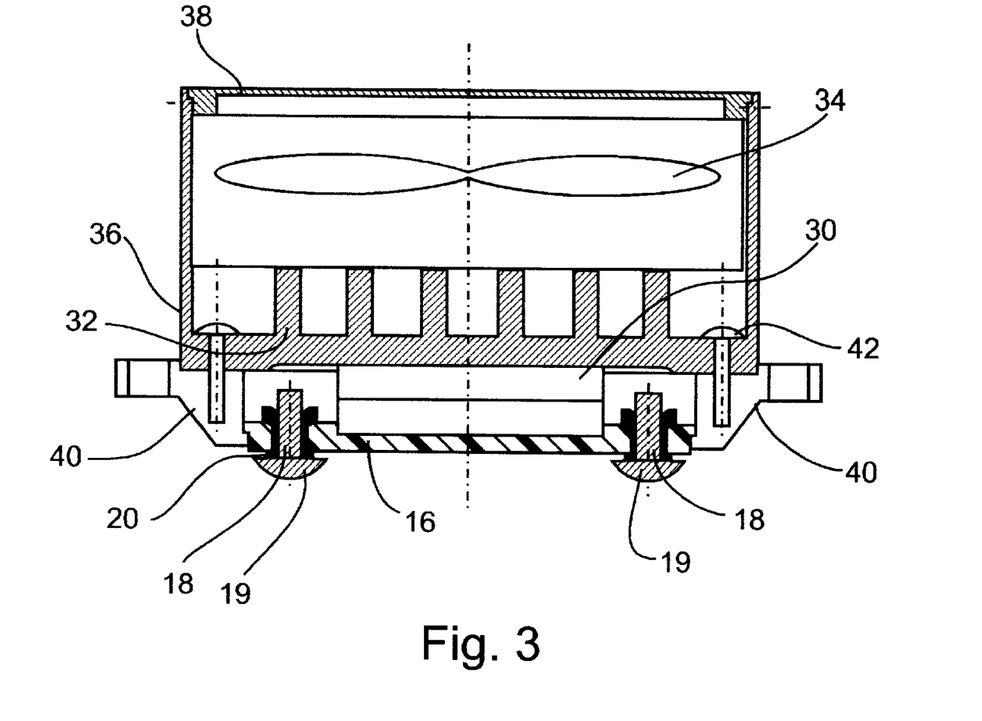
FIG. 3 is a more detailed side view of the device of FIG. 1.

Reference is now made to FIG. 3, which is a sectional view from one side of a device operable in accordance with the embodiment of FIG. 1. Parts that are identical to those shown above are given the same reference numerals and are not referred to again except as necessary for an understanding of the present embodiment. In FIG. 3, the heat transfer medium 16, for placing in contact with the treatment area is thermally coupled with a thermoelectric module 30. The thermoelectric module 30 is preferably connected on its other side to a heat sink 32 and to a fan 34 or to a small refrigeration unit. The combination of the thermoelectric module 30, the heat sink 32 and the fan 34 preferably comprises a compact and effective temperature driving element 22. Electrodes 18 are preferably also thermally coupled to the heat transfer medium 16, and, as described above, the electrodes 18 are electrically isolated from the heat transfer area by respective dielectric layers 20, preferably made of aluminum oxide. An outer part 36 of the heat sink 32 serves as a housing for the arrangement. Preferably, the heat sink—housing—cover arrangement 32, 36, 38, is provided with holes for airflow.

It is noted that the heat sink arrangement provides two methods for heat removal, natural convection from the casing part 36 of the heat sink 32 and forced convection from the inner side due to the fan. A connector part 40, having screws 42, is mounted between the heat transfer medium 16 and the heat sink 32 to define a fit between the medium 16, the heat arrangement and the thermoelectric module 30. The connector part 40 preferably has low thermal conductance so as to preserve the temperature distance between the heat sink 32 and the medium 16. The connector part is preferably in contact with the patient when in use and preferably also in contact with the medium 16 and with the electrodes 18. The connector part 40 is thus preferably electrically isolated at least from the electrodes 18.

The connector 40 preferably also carries strap hooks for attaching the strap 14.

Figure 4:
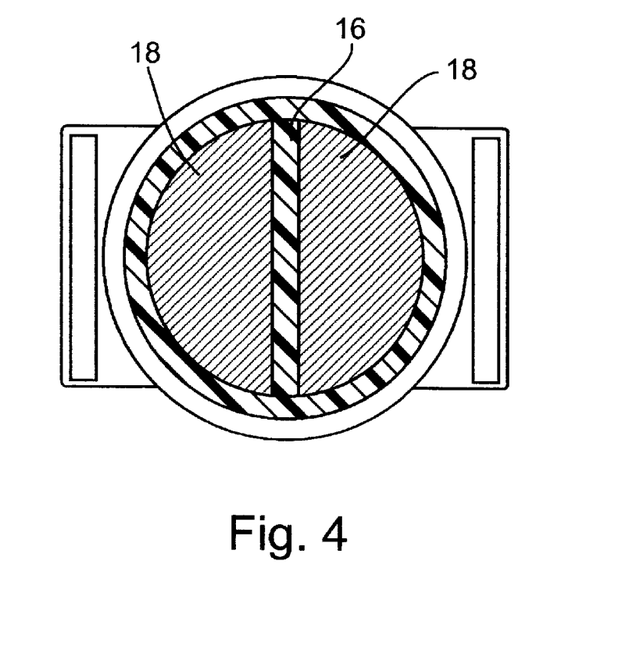
FIGS. 4–6 are views of possible electrode layouts in the device of FIG. 1.
Figure 5:
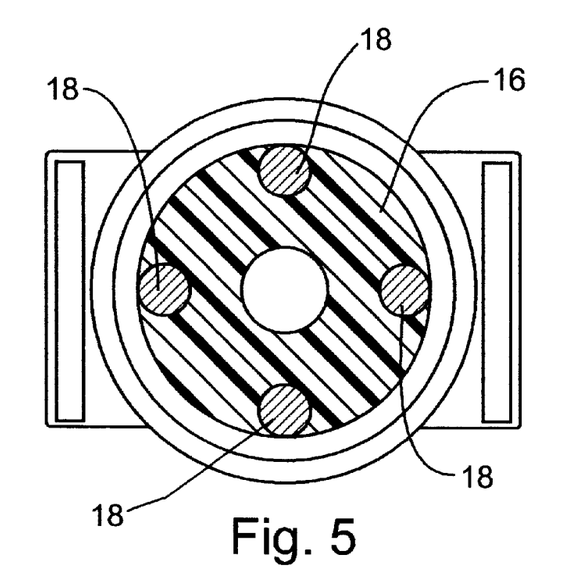
Figure 6:
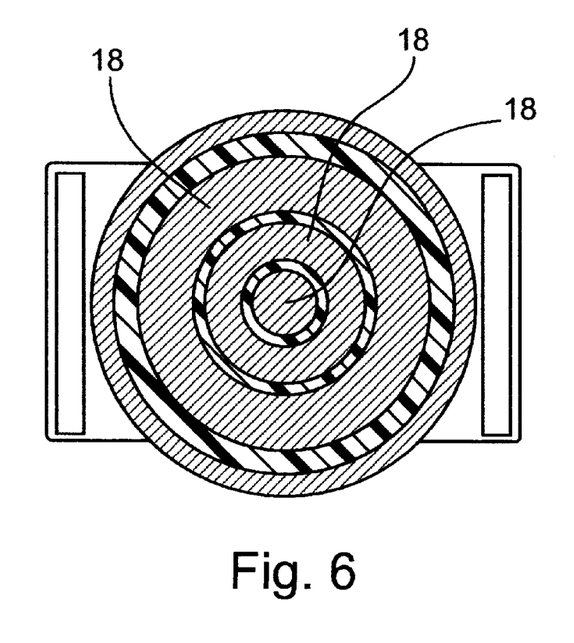

Reference is now made to FIGS. 4, 5 and 6, which are views from below of the heat transfer medium 16 with electrodes 18 inserted therein. As mentioned above, using the present invention, it is possible to apply heat and electrical stimulation to a treatment area even if the area is relatively small. In the present embodiments it is possible to provide different electrode layouts on the heating area. As mentioned above, the electrodes are thermally coupled to the heat transfer medium 16 such that heat is transferred over all of the lower surface of the device. Different configurations of electrode allow for precise applications of electric stimulation over the treatment area.

FIG. 4 shows a configuration in which two electrodes 18 are arranged to supply electrical stimulation to substantially all of the treatment area 16. FIG. 5 shows an arrangement having four small electrode regions 18 arranged circumferentially around the treatment area 16. FIG. 6 shows an arrangement in which three electrodes 18 are arranged radially about a center of the treatment area 16, again applying electrical stimulation over substantially all of the treatment area.

Figure 7:
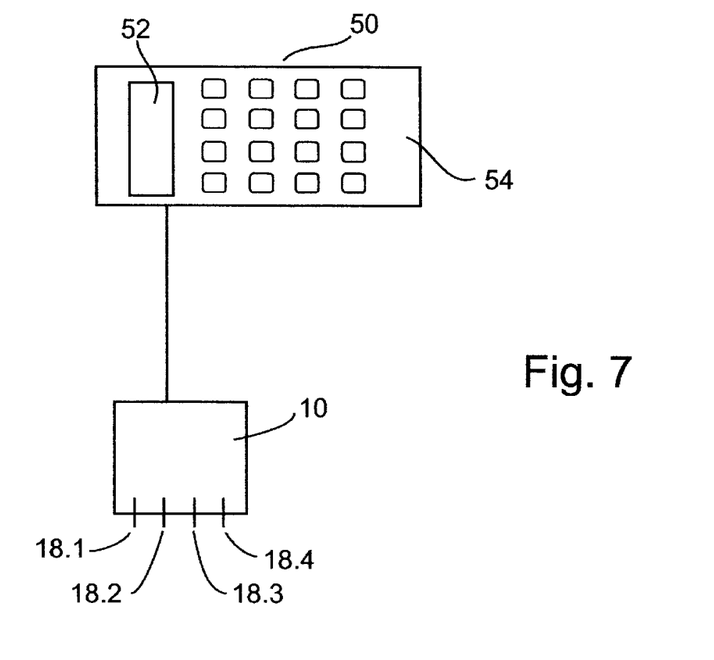
FIG. 7 is a simplified diagram showing how programming of the device may be carried out using a programming unit.

Reference is now made to FIG. 7, which is a simplified block diagram illustrating programming of an embodiment of a physiotherapeutic device according to the present invention. Parts that are identical to those shown above are given the same reference numerals and are not referred to again except as necessary for an understanding of the present embodiment. In the embodiment of FIG. 7, a physiotherapeutic device 10, having four electrodes 18.1 . . . 18.4, is connected to an external programming unit 50. The programming unit 50 preferably comprises a screen 52 and keyboard 54 and allows a user to enter a program comprising desired combinations of temperature levels and changes and current and voltage levels and changes. Each one of the electrodes is preferably programmable independently.

For example a typical program may comprise five minutes at a high temperature followed by five minutes at a low temperature, all the while producing a square waveform at each of the four electrodes.

Figure 8:
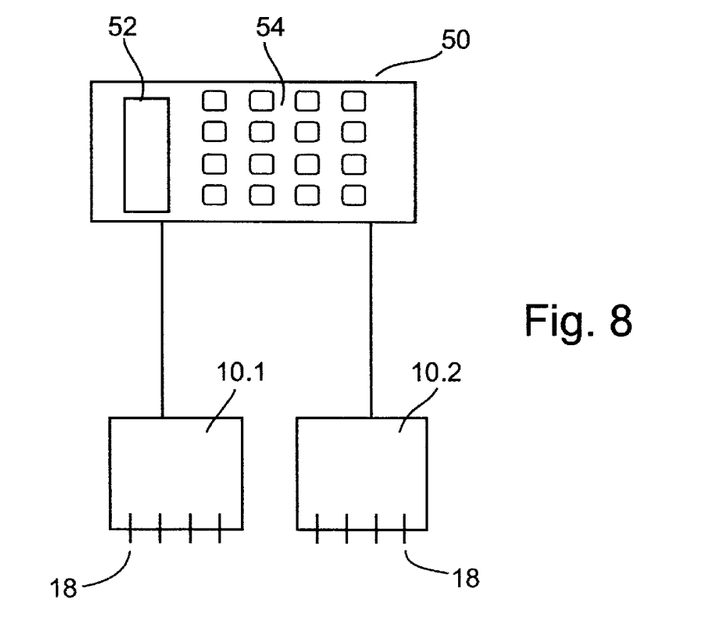
FIG. 8 is a simplified diagram showing how programming of a plurality of devices may be carried out using a programming unit.

Reference is now made to FIG. 8 which is a simplified block diagram illustrating a variation of the programming shown in FIG. 7. In the embodiment of FIG. 8, two physiotherapeutic devices are connected together to the programming unit 50. They are jointly programmed for simultaneous use on a patient, for example where treatment is required on two localized areas. Again the electrodes 18 are preferably programmable independently, and the temperatures of the two devices are preferably likewise programmable independently. Preferably, more than two devices can be connected to the programming unit 50 as required. When a single device is used, the distance between electrodes is predefined, a preferred range of distances between electrodes for effective operation being between 5 mm and 50 mm.

In accordance with the above embodiments there is thus provided a physiotherapeutic device in which electrodes are integrated with a low heat capacity heat transfer medium. The electrodes are electrically insulated from each other and from the heat transfer medium whilst being thermally coupled to the heat transfer medium. Thus it is possible to provide flexible thermotherapy in conjunction with electrotherapy to a treatment area, even in cases where the treatment area may be relatively small.

Pain relieving preparations absorbable through the skin are widely known. One use of the above embodiments involves placing a pad comprising such a preparation on the treatment area and then applying a physiotherapeutic device embodying the present invention to the pad. The application of heat and electric stimulation improves absorption of the substance through the skin.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

It will be appreciated by persons skilled in the art that the present invention is not limited to what has been particularly shown and described hereinabove. Rather the scope of the present invention is defined by the appended claims and includes both combinations and subcombinations of the various features described hereinabove as well as variations and modifications thereof which would occur to persons skilled in the art upon reading the foregoing description.

What is claimed is:

1. A physiotherapeutic device for concurrently providing heat transfer and electrical stimulation to a localized treatment area, the device comprising:
   a heat transfer medium for placing in contact with said treatment area, said heat transfer medium comprising a thermo-conductive material and having a heat capacity such that said device is operable to change a temperature gradient within said heat transfer medium from one able to induce a burn to a safe temperature substantially within a minute,
   at least one electrode located within said heat transfer medium, said electrode comprising a thermo-conductive material, and
   a dielectric layer for providing electrical isolation between said at least one electrode and said heat transfer medium, said dielectric layer comprising a thermo-conductive material.

2. A physiotherapeutic device according to claim 1, wherein said heat transfer medium has an external dielectric covering.

3. A physiotherapeutic device according to claim 2, wherein said electrodes are thermally coupled to said heat transfer medium via said dielectric layer.

4. A physiotherapeutic device according to claim 1, having a temperature range of at least 40 degrees C. between a maximum treatment temperature and a minimum treatment temperature, and being operable to permit said heat transfer medium to alternate between said maximum and said minimum treatment temperatures in substantially one minute.

5. A physiotherapeutic device according to claim 1, having a plurality of electrodes integrally located within said heat transfer medium.

6. A physiotherapeutic device according to claim 5, each electrode being programmable independently to provide electrical stimulation.

7. A physiotherapeutic device according to claim 5, said electrodes and said heat transfer medium being programmable separately to provide a combined regime of electrical and heat treatment.

8. A physiotherapeutic device according to claim 5, wherein said electrodes are programmable to provide electrical stimulation selectably as a constant voltage level, a constant current level, and a selectable waveform at a selectable frequency.

9. A physiotherapeutic device according to claim 1, programmable remotely over an electronic network.

10. A physiotherapeutic device according to claim 1, said electrode having a thermal diffusivity substantially similar to a thermal diffusivity of said heat transfer medium.

11. A physiotherapeutic device for concurrently applying heat, cooling, and electrical stimulation to a localized treatment area, the device comprising a heat transfer medium for placing in contact with said treatment area and at least two electrodes integrally located within said heat transfer medium and electrically insulated therefrom.

12. A physiotherapeutic device according to claim 11, having a dielectric layer intervening between at least one electrode and said heat transfer medium.

13. A physiotherapeutic device according to claim 12, wherein said dielectric layer is a heat conducting layer.

14. A physiotherapeutic device according to claim 12, wherein said dielectric layer is a heat conducting layer.

15. A physiotherapeutic device according to claim 11, having a temperature range of at least 40 degrees between a maximum treatment temperature and a minimum treatment temperature, and having a combination of heat control power, heat transfer medium size and heat transfer medium thermal diffusivity selected to permit said heat transfer medium to alternate between said maximum and said minimum treatment temperatures in substantially one minute.

16. A physiotherapeutic device according to claim 11, having a plurality of electrodes, each electrode being programmable independently to provide electrical stimulation.

17. A physiotherapeutic device according to claim 11, said electrodes and said heat transfer medium being programmable separately to provide a combined regime of electrical and heat treatment.

18. A physiotherapeutic device according to claim 11, wherein said electrodes are programmable to provide electrical stimulation selectably as a constant voltage level, a constant current level, and a selectable waveform at a selectable frequency.

19. A physiotherapeutic device according to claim 18, programmable remotely over an electronic network.

20. A physiotherapeutic device according to claim 11, wherein said electrodes are thermally coupled to said heat transfer medium.

21. A physiotherapeutic device according to claim 11, wherein said heat conducting medium has an outer dielectric coating.

* * * * *